(12) United States Patent
Bergendahl

(10) Patent No.: US 9,161,863 B2
(45) Date of Patent: Oct. 20, 2015

(54) ABSORBENT ARTICLE COMPRISING A SHAPED ELEMENT AND A METHOD OF MAKING SUCH

(75) Inventor: Magnus Bergendahl, Mölnlycke (SE)

(73) Assignee: SCA HYGIENE PRODUCTS AB, Gothenburg (SE)

( * ) Notice: Subject to any disclaimer, the term of this patent is extended or adjusted under 35 U.S.C. 154(b) by 180 days.

(21) Appl. No.: 13/882,680

(22) PCT Filed: Jan. 26, 2011

(86) PCT No.: PCT/EP2011/051052
§ 371 (c)(1),
(2), (4) Date: Apr. 30, 2013

(87) PCT Pub. No.: WO2012/100823
PCT Pub. Date: Aug. 2, 2012

(65) Prior Publication Data
US 2013/0218119 A1    Aug. 22, 2013

(51) Int. Cl.
*A61F 13/471* (2006.01)
*A61F 13/56* (2006.01)
(Continued)

(52) U.S. Cl.
CPC ....... *A61F 13/4702* (2013.01); *A61F 13/15699* (2013.01); *A61F 13/15756* (2013.01); *A61F 13/471* (2013.01)

(58) Field of Classification Search
CPC .......................... A61F 13/4702; A61F 13/471
USPC ..................................... 604/385.31
See application file for complete search history.

(56) References Cited

U.S. PATENT DOCUMENTS 4,216,773 A * 8/1980 Ryan ............................. 604/365
5,580,411 A   12/1996 Nease et al.
(Continued)

FOREIGN PATENT DOCUMENTS

CN          1568168 A       1/2005
CN       101312701 A      11/2008
(Continued)

OTHER PUBLICATIONS

International Search Report (PCT/ISA/210) issued on Sep. 29, 2011, by the European Patent Office as the International Searching Authority for International Application No. PCT/EP2011/051052.
(Continued)

*Primary Examiner* — Susan Su
(74) *Attorney, Agent, or Firm* — Buchanan Ingersoll & Rooney PC

(57) ABSTRACT

An absorbent article, which comprises a fastening element for the absorbent article for fastening the absorbent article to underpants or a stiffening element for providing a relatively stiff region of the absorbent article and for defining a collapse prone portion of the absorbent article to shape the absorbent article as desired. The element defines a Y- or X-shape and comprises a first piece of material defining a bend and a second piece of material defining a bend, wherein the first and second pieces of material and their bends together define the Y or X shape of the element. The first and second pieces define a generally V- or U-shape so that each of the first and second pieces has first and second legs extending from a point of the V-shape or a bight of the U-shape, wherein the second legs respectively provide first and second arms of the Y- or X-shape of the element, and wherein the first legs either together provide a third arm of the Y-shape or respectively provide third and fourth arms of the X-shape.

21 Claims, 9 Drawing Sheets

(51) Int. Cl.
  *A61F 13/47* (2006.01)
  *A61F 13/15* (2006.01)

(56) References Cited

U.S. PATENT DOCUMENTS

| | | | |
|---|---|---|---|
| 5,683,533 A * | 11/1997 | Keighley et al. | 156/204 |
| 5,849,003 A * | 12/1998 | Olsen et al. | 604/387 |
| 5,858,011 A * | 1/1999 | Brown et al. | 604/385.23 |
| 5,993,431 A * | 11/1999 | McFall et al. | 604/385.24 |
| 6,565,548 B1 * | 5/2003 | Glaug et al. | 604/385.03 |
| 7,291,136 B1 * | 11/2007 | Drevik et al. | 604/385.03 |
| 7,780,643 B2 | 8/2010 | Persson | |
| 8,702,671 B2 * | 4/2014 | Tsang et al. | 604/385.21 |
| 8,790,325 B2 * | 7/2014 | Sauer et al. | 604/385.22 |
| 2003/0125699 A1 | 7/2003 | Drevik et al. | |
| 2003/0125700 A1 | 7/2003 | Drevik | |
| 2004/0111073 A1 | 6/2004 | Hermansson et al. | |
| 2005/0004547 A1 * | 1/2005 | Lavash | 604/385.16 |
| 2005/0143703 A1 | 6/2005 | Persson | |
| 2007/0142815 A1 * | 6/2007 | Macura et al. | 604/389 |
| 2008/0319411 A1 * | 12/2008 | Mortensen et al. | 604/387 |
| 2010/0228217 A1 | 9/2010 | Harsjo | |
| 2011/0319857 A1 | 12/2011 | Drevik et al. | |

FOREIGN PATENT DOCUMENTS

| | | |
|---|---|---|
| JP | 59-196484 U | 11/1984 |
| JP | 11-503032 A | 3/1999 |
| JP | 11-510071 A | 9/1999 |
| JP | 2008-289947 A | 12/2008 |
| WO | WO 86/06620 A1 | 11/1986 |
| WO | 96/11147 A1 | 4/1996 |
| WO | WO 96/24319 A1 | 8/1996 |
| WO | 97/04730 A2 | 2/1997 |
| WO | 98/22061 A1 | 5/1998 |
| WO | 01/17474 A1 | 3/2001 |
| WO | 02/087483 A1 | 11/2002 |
| WO | 03/047484 A1 | 6/2003 |
| WO | 2010/101499 A1 | 9/2010 |
| WO | 2010/101501 A1 | 9/2010 |
| WO | 2010/101502 A1 | 9/2010 |

OTHER PUBLICATIONS

Written Opinion (PCT/ISA/237) issued on Sep. 29, 2011, by the European Patent Office as the International Searching Authority for International Application No. PCT/EP2011/051052.

International Preliminary Report on Patentability (PCT/IPEA/409) issued on Feb. 7, 2013, by the European Patent Office as the International Searching Authority for International Application No. PCT/EP2011/051052.

An English Translation of the Office Action (Notification of the First Office Action) issued on Jun. 23, 2014, by the State Intellectual Property Office (SIPO) of the People's Republic of China in corresponding Chinese Patent Application No. 201180056596.1. (6 pages).

Office Action (Notice of Reasons for Rejection) issued on Jan. 5, 2015, by the Japanese Patent Office in corresponding Japanese Patent Application 2013-550769. (6 pages).

* cited by examiner

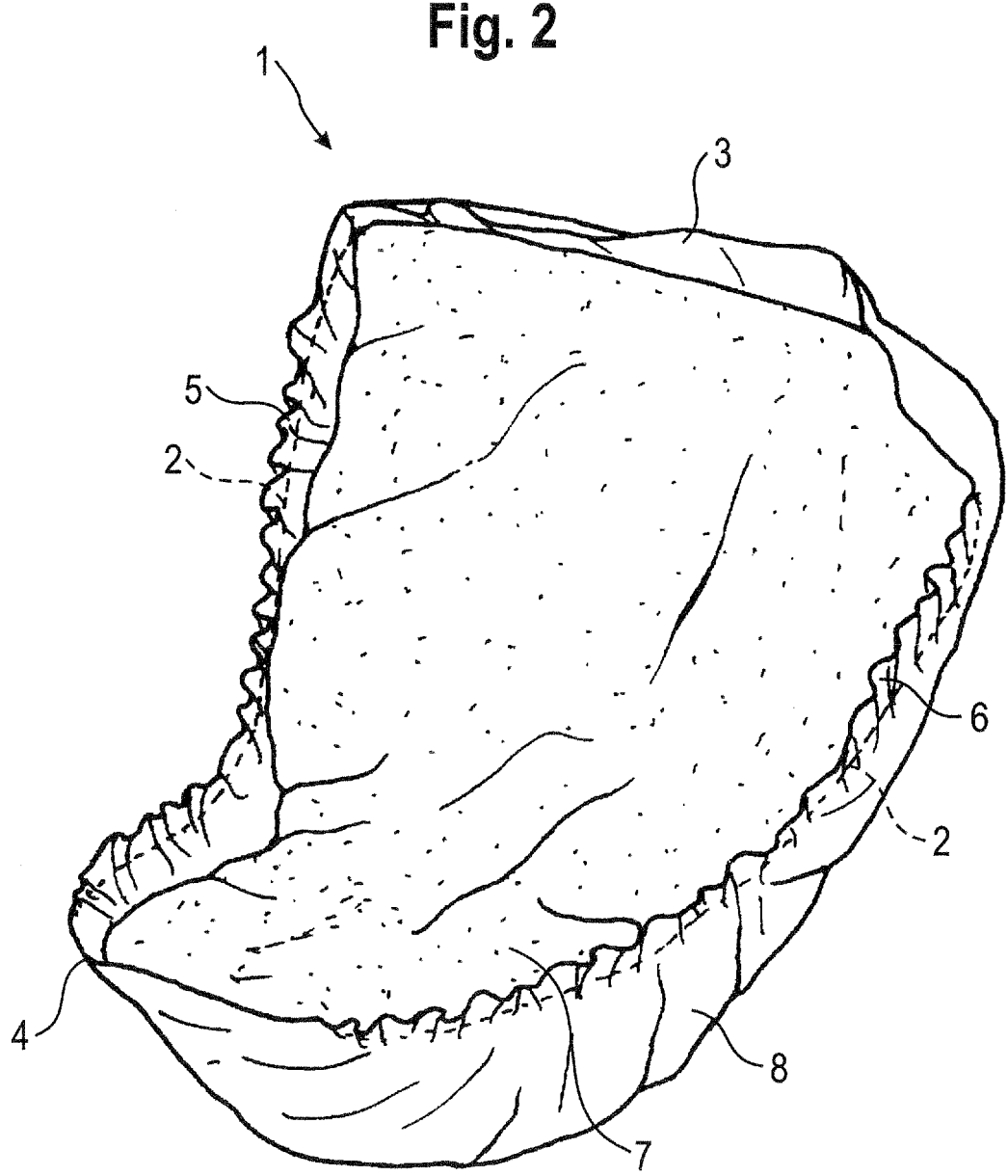

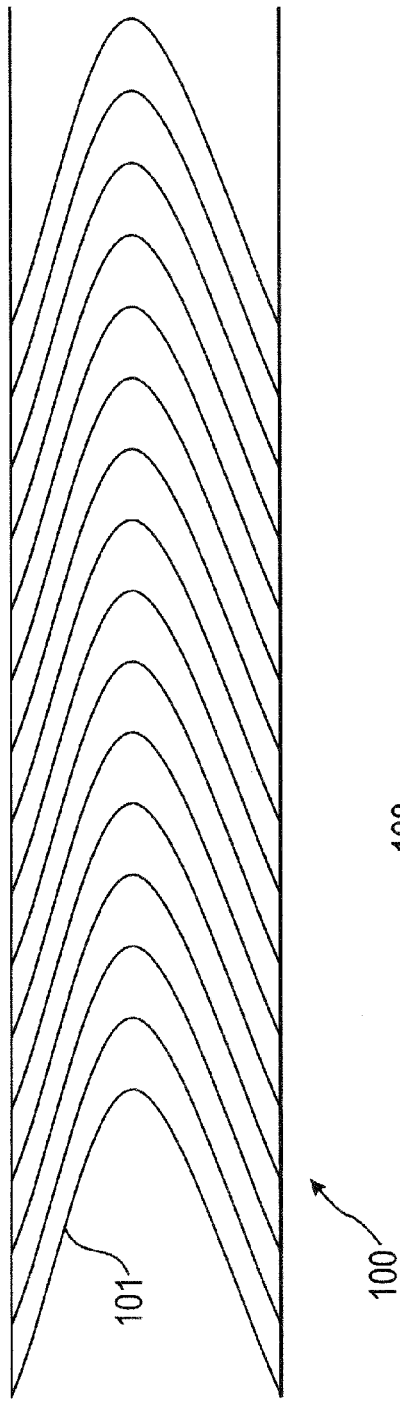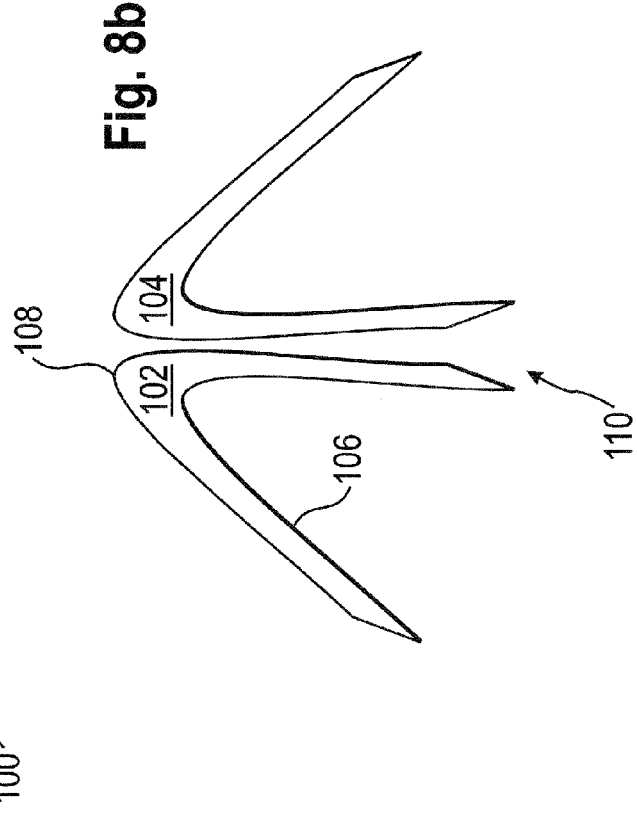

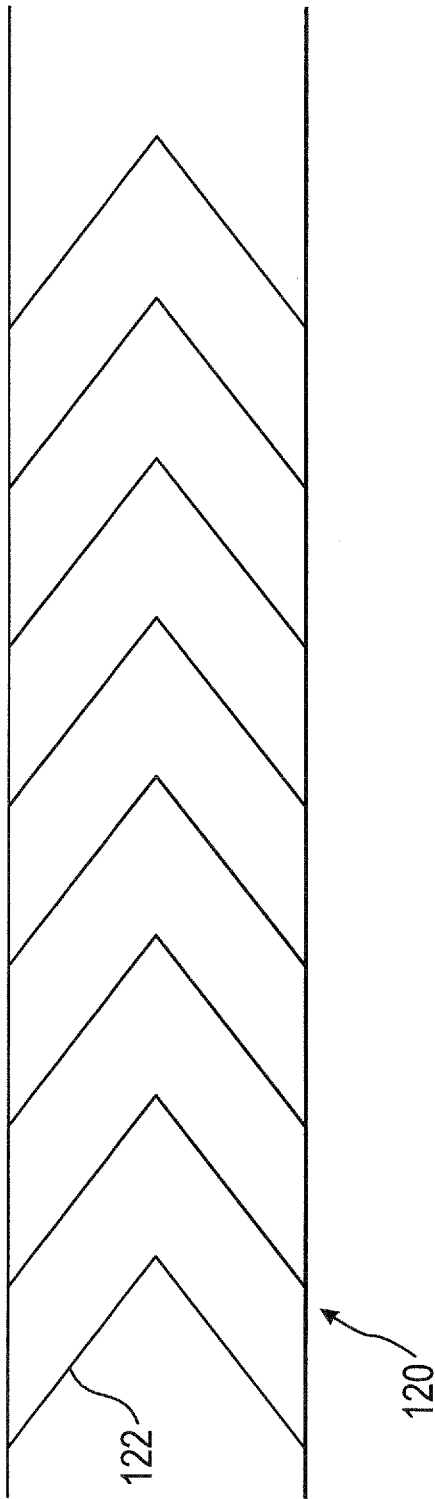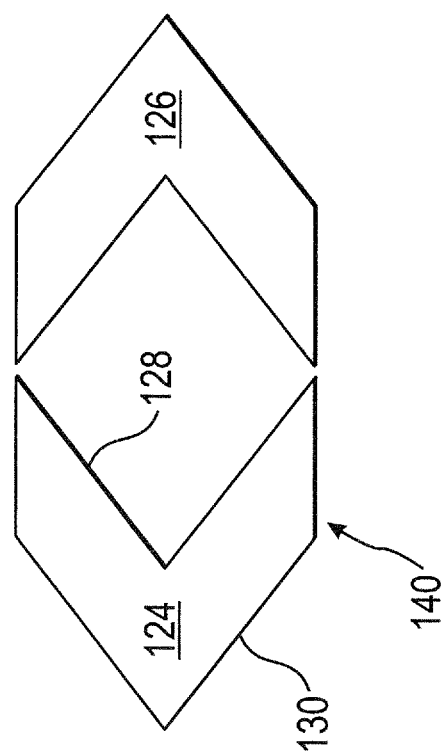

ABSORBENT ARTICLE COMPRISING A SHAPED ELEMENT AND A METHOD OF MAKING SUCH

FIELD OF THE INVENTION

The present invention is concerned with an absorbent article and a method of making an absorbent article that comprises a fastening element or a stiffening element for shaping the absorbent article.

BACKGROUND OF THE INVENTION

An absorbent article, such as a sanitary towel, is known from U.S. Pat. No. 7,156,832 that has a stiffening element that is relatively stiff as compared to other layers of the absorbent article such as an absorbent core, a body side layer and a liquid impermeable outer layer, wherein the body side layer and the outer layer encase the absorbent core. The absorbent article is hourglass shaped in plan view. The stiffening element has a hole therethrough that is positioned over a longitudinal central line that collapses under lateral forces during use to provide the article with a desired three dimensional shape. The stiffening element is disclosed as being, in a preferred option, an absorbent core comprising superabsorbent. It results in material wastage to stamp a hole out of the stiffening element.

A male incontinence guard sold under the Trade name Tena for Men™ Level 1 or Level 2 has a a bodyside liner, an outer liner and an absorbent pad disposed therebetween. The guard is generally triangular shaped when laid out flat. The base of the triangle is worn closer to the waist of the user, while the point of the triangle is positioned more towards the area between the legs of the user. This shape of article is more comfortable for the wearer and offers liquid retention benefits. The outer liner has rectangular strips of adhesive tape attached to it that are covered by a release liner. To wear, the release liner is peeled away and the adhesive strips serve to removably fix the guard in position on underpants of a wearer. Alternative shapes for the adhesive tape may be desirable that provide improved fastening coverage of the triangular shaped absorbent article. Such alternative shapes would optimally maintain material use efficiency (lack of waste trimmings) of rectangular strips.

SUMMARY

It has been found that it may be desirable to form a stiffening element or fastening element or other element to include a shape such as a Y-shape or an x-shape. Such a Y shape is a shape including three arms extending from a point of intersection of the three arms, wherein the arms have an intersecting end and opposed free ends that are spaced apart. An x-shape is one having four arms extending from a generally central point of intersection, wherein the arms have an intersecting end and an opposed free end and the free end of each arm is spaced apart. For example, in the male incontinence guard described above, a Y-shaped fastening element is able to be formed such that the free ends of the arms extend toward the corners of the base of the triangle of the guard, while the free end of the leg extends toward the point of the triangle. This will provide coverage of the corner portions of the triangle shaped guard by a single fastening element. In the hour glass shaped absorbent article described above, an x-shaped fastener is able to reach to each of the four corner portions for optimally securing the absorbent article to an underpant. In the sanitary towel described above, a Y-shaped stiffening element may be useful in that the leg of the Y can extend longitudinally and the gap between the arms of the Y can partially define the opening of the stiffening element so as to define a collapsible portion providing a desired three dimensional shape to the sanitary towel.

In the above, there is offered specific examples for use of a Y- or X-shaped fastener or stiffening element. There are and will be other absorbent article applications where an element defining a shape other than a strip-like rectangle, such as a Y-shape or an X-shape, will desirably be employed.

A problem with cutting complex shaped elements (shaped other than in strip shape), such as a Y- or X-shaped element, is that it involves a significant amount of waste material as a result of a nesting mismatch in adjacent elements. Stamping such complex shapes out of a web of material results in too much waste for productions efficiency purposes. Accordingly, it would be desirable to provide a method of manufacturing an absorbent article having an element defining a desirably shaped portion that is made with reduced waste. An absorbent article comprising a fastening element or stiffening element so made would also be desirable.

The present disclosure provides a method of manufacturing an absorbent article comprising an element applied thereto that defines a shape, the method comprising providing first and second pieces of planar material, wherein the first and second pieces define a bend when viewed in plan, and forming the absorbent article to have the first and second pieces applied thereto, wherein the pieces are arranged together to together define the shape of the element.

This can save material since a complex shape can be broken down into first and second pieces defining a bend. Such pieces may be more susceptible to being cut from a web of material than the complex shape. Accordingly, there can be reduced waste trimmings as compared to a method producing the complex shape from a single piece.

The shape may have an intersecting region where the first and second pieces are substantially in contact and at least one arm, preferably a plurality of arms, extending away from the intersecting region or point. Examples of such shapes are X and Y shapes, which have respectively four and three arms extending away from an intersecting point. To create such shapes, outside edges of the bends of the first and second pieces can be brought into substantial contact. Alternatively, the shape may circumscribe a space. Examples of such shapes are 2D four-sided polygonal shapes such as a 2D diamond shape. In this case, the shapes can be formed by facing the inside edge of the bends of the first and second pieces toward one another and the outside edges away from one another. The inside edges of the first and second pieces will be brought close enough together that the space circumscription is substantially continuous.

The x-, y- and 2D four sided polygonal shapes discussed above are all considered to have application in forming a stiffening or fastening element for an absorbent article. Other shapes of interest are m- or T-shapes, which, like the Y-shape, have three arms.

In considering whether first and second pieces are arranged together, the pieces should be in substantial contact. Production accuracy may, however, mean that there is a maximum gap where the first and second pieces are brought into substantial contact of around 2 mm, but perhaps going up to 5 mm.

Preferably, the outside edges of the bends of the first and second pieces are brought into substantial contact. Alternatively, the inside edges of the bends of the first and second pieces are brought into facing relation so as to enclose a space.

The inside edges of the bends of the first and second pieces could also be brought into substantial contact to define interesting shapes.

The providing step may comprise cutting first and second pieces of material from at least one web of material, preferably a first web of material. In the event of cutting the first and second pieces of material from a first web of material, the bends of the first and second pieces of material may be cut so as to face in the same direction and then rotated relative to one another so that the bends face one another, in opposed directions, in the arrangement as applied to the absorbent article.

Bent pieces of material that are rotated to form a shape when back to back are able to nest with one another when the bends are front to back. Accordingly, by cutting the bent pieces from the web when they are facing in the same direction, the pieces are in a relatively nested configuration. That is, the bends are front to back as they are being cut, which allows nesting of the shapes and thus reduces loss of material when the bends are cut.

The relative rotation of the pieces of material may be achieved by flipping one of the pieces relative to the other one and/or rotating at least one of the pieces while maintaining the same side of the piece facing up. In the latter form, both pieces could be rotated in that one piece is rotated left and the other piece right or one piece could be held stationary, while the other piece is rotated. If a fastening means is provided on one surface of the element, then rotation by flipping will not result in the fastening means facing up in the same sense. Accordingly, rotation without flipping in a left or right direction would be the appropriate method when the pieces have a right way up.

Whether or not a piece of material has a bend can be determined from a central line between opposing lateral edges of a generally elongate piece of material. If the central line defines a straight line, it is not bent. If it defines a linear line with an angle between a first portion of the line and a second portion of the line, or a curve, or a curvilinear path, then the piece defines a bend.

Preferably, the outer edge of the bend of the first piece and the outer edge of the bend of the second piece are brought into facing relation, preferably substantially into contact, in forming the absorbent article and defining the shape of the element. Preferably, at the location where the bends are brought together, there is located a point of intersection of arms of the shape. Preferably, each piece defines substantially one half of the shape. Also preferably, in defining a Y-, T- or m-shape of the element, the first piece of material defines a first arm of the Y-, T- or m-shape, the second piece of material defines a second arm of the Y-, T- or m-shape and the first and second pieces together define a third arm of the Y-, T or m-shape, preferably substantially one half of the third arm of the Y, T or m shape each. In forming an X-shape of the element, a line can be drawn through the intersection of the four arms of the X-shape so that a first pair arms are on one side of the line and a second pair of arms are on the other side of the line, wherein the first piece of material defines the first pair and the second piece of material defines the second pair.

The first and second pieces of material may define first and second strip portions connected by a bend. In the case of a Y-shape or m-shape or T-shape of an element, the first portions are brought together to jointly provide a third arm of the shape, while the second portions provide respective first and second arms of the shape of the element. In the case of an X-shape of an element, the first and second portions of a first piece provide respective arms on one side of the X-shape of the element and the first and second portions of a second piece provide respective arms on another side of the X-shape. The first and second pieces are preferably rotated so as to bring the bends into facing relation to define arms of the shape.

The element may as a whole be a general Y-, T, X-, m- or four sided polygonal shape so formed or the element may define the Y-, X-, T-, m- or four sided polygonal shape as a part of the whole element. This is perhaps best understood with reference to the embodiment of FIG. 4, where first and second pieces 30, 32 are shown that define first and second Y-shapes 80, 82, as shown by the alternatively shaded Y-shapes, of the element 28 and further define shapes other than a Y-shape at opposed terminal ends of the element.

The bend may be between two linear portions of the pieces or the portions may be curved to define the bend. In one embodiment, the pieces of material define a general V-shape or a general U-shape. If the V-shape of the pieces of material or the U-shape of the pieces of material have the legs of the V- or U-shape relatively broadly spread apart, then a Y- or T shape can be made by relatively rotating the Vs or Us so that the bends face one another. Two legs of the Vs or Us will jointly form one arm of the Y or T, while the other two legs of the Vs or Us will form the arms of the Y or T. If the V-shape of the pieces of material have their legs relatively closely spaced together, then an m-shape can be made by relatively rotating the Vs to bring their legs together. Two legs of the Vs will jointly form a middle arm of the m-shape, while the other two arms of the Vs will respectively form the outside of the m-shape. Alternatively, two legs of a V- or U-shape of a first piece of material will form two arms of the X-shape, while two legs of the other V- or U-shape will form the other two arms of the X-shape. The V- or U-shapes of the respective pieces are brought together so that the point of the V-shape or the bight of the U-shape of the respective pieces together define the intersection of the arms of the Y-shape or the X-shape.

The Y shape of the element does not have to be a perfect Y. That is, the angle between the arms of the Y can be varied and each arm of the Y may be angled from a line bisecting the other two arms of the Y. Further, the first and second pieces do not necessarily have to contact each other, but they do in a preferred embodiment. That is, there may be a slight gap between the first and second pieces in the form in which they are applied to the absorbent article, particularly as a result of limitations in placement accuracy during manufacture of such an article (as discussed above). The gap may be continuous or an arm of the Y defined by the first and second pieces may be bifurcated.

Preferably, the first and second pieces are arranged in the absorbent article on either side of a line of symmetry for the first and second pieces. That is, the first and second pieces are a mirror image of one another when arranged on the absorbent article about the line of symmetry. Preferably, the line of symmetry is arranged longitudinally with respect to the absorbent article (from rear waist region to front waist region). Yet more preferably, the line of symmetry is arranged along a central longitudinal line of the absorbent article.

In the embodiments described above where the first and second pieces are cut from at least one web of material, the cutting of the first and second pieces is preferably done in the width direction of the at least one web.

Preferably, the at least one web of material is at least one continuous web of material that is continuously cut into pieces of material having bends facing in the same direction. Preferably, where the at least one web is a first web of material, the first and second pieces of material are repeatedly taken and relatively rotated so that the bends are facing each other to thereby define the shape of the element. The cutting may be performed by a cutting roll having one or more cutting blades defining opposing edges of each piece cut.

The shape of the element can be made so as to minimize waste of web material. The at least one web of material may be cut so that the pieces nest with one another with minimal gap between adjacent cut pieces. Thus, one could reconstruct the at least one web of material from the cut pieces with minimal gaps since there are minimal trimmings. Put another way, each of the first and second pieces are cut to have an outside edge of the bend and an inside edge of the bend. The outside edge of the first and the second piece is shaped to fit the inside edge of the first and second piece. Preferably, the outside edge of each piece is a match of the inside edge, only spaced from one another. They may not, alternatively, match perfectly. That is, there may be some trimming produced during the cutting process. Additionally or alternatively, some trimming may be produced as a post processing step to the cutting process that cuts the web material into respective pieces.

In terms of manufacturing and in the endeavor of minimizing waste material, the web of material is cut into successive pieces of material having the bend facing in the same direction, wherein a rearward edge of succeeding bends defines a forward edge of preceding bends. Thus, the rearward edge of succeeding bends mates with the forward edge of preceding bends so that the continuous web of material is cut with the pieces nesting.

Preferably, successive pieces of material are nested. That is, the degree of conformance of a preceding piece having a bend to a succeeding piece having a bend is to such an extent that the web of material is cut with as little waste of web material, in terms of area of material trimmed away from the pieces divided by area of the web from which the pieces are cut, as 0.3, 0.2, 0.1, 0.05, 0.04, 0.03, 0.02, 0.01 or even more preferably about 0. When there is 0 waste, the web is cut into perfectly nesting pieces. Thus, each piece is made by two identical cut lines defining the outside and inside edges of the bend of the piece and the cut line for a preceding piece provides the cut line for a succeeding piece.

The element defining the shape may be applied to the absorbent article in a number of ways. The first and second pieces may be attached e.g. adhered, together so as to define the shape prior to application to the absorbent article or the shape may be fixed when the element defining the shape is applied, e.g. adhered, to the absorbent article, wherein prior to that the pieces would still be moveable relative to one another if manipulated. The element may be applied to absorbent article precursor material, such as a bodyside liner, an absorbent layer, an outer cover or a laminate thereof, or it may be applied to a preformed absorbent article.

The element may be a fastener element defining the shape. The fastener element may have any known fastener element application in absorbent articles. Thus, the fastener element may be for fastening parts of a waist region of the absorbent article together to secure the absorbent article about the waist of a wearer. Preferably, however, the fastener element is applied to form an outer layer of the absorbent article in use for removably fastening the absorbent article to underpants. The fastener element may be an adhesive strip type fastener, wherein a release liner covers the fastening element. Preferably, the fastening element is a hook type fastener, preferably for fastening to underpants in use. The hook type fastener is configured to provide sufficient fastening to fasten the absorbent article to underpants, yet to be low in abrasiveness so as not to ruin fabric of the underpants even after repeated use.

In one embodiment, the fastening element is applied to an absorbent article having a relatively narrow crotch portion for location between the legs of a wearer and a relatively wide waist portion for location nearer the waist of the wearer. Preferably, the absorbent article is an absorbent incontinence liner for men in that it defines a generally triangular shaped perimeter when flattened and is configured to form a more bowled shape when worn.

Preferably, the element defines a Y shape and arms of the Y shape of the element extend respectively to corner portions of the relatively wide waist portion and an arm of the Y shape of the element extends to the relatively narrow crotch portion and extends substantially along a longitudinal centre line of the article. The Y shape of the element is orientated to provide good coverage of the absorbent article with the fastening element.

The corner portions of the absorbent article are held to the underpants by the arms, respectively, while the centre of the narrow portion for accommodating legs of the wearer is held by the other arm of the Y shape. Such extensive coverage of the absorbent article is achieved in a relatively straight forward manufacturing process because the Y shape is longitudinally orientated. The extensive coverage achieved by the Y shape of the fastening element may well allow the use of a low adherence per square centimeter fastener, which may be less abrasive to fabric of the underpants.

In another embodiment, the element is a stiffening element for stiffening a portion of the absorbent article to which it is applied and thereby providing a less stiff region of the absorbent article at locations where the stiffening element is absent. The less stiff region is thus more prone to collapse when the absorbent article is worn in order to shape the absorbent article as desired. The collapse prone portion will define a peak and valley structure when it collapses upon being worn, thereby increasing a Z directional shape in a region of the absorbent article. The stiffening member may be a dedicated stiffening member or may be provided by stiffened absorbent core pieces.

Preferably, a gap between first and second arms of the Y- or X-shape of the element defines a first collapse prone portion of the absorbent article. The first collapse prone portion may be located for positioning between buttocks of a wearer to stabilize a portion of the article relative to the wearer or it may be positioned for being collapsed by squeezing between the legs of the wearer to create increased depth in a region of the article for comfort or to define a bowl in the absorbent article for improved liquid retention. In either case, a third arm of the Y shape of the element is positioned substantially along a longitudinal line of the article and first and second arms of the element extend in opposing lateral directions from the longitudinal line. The first and second arms may be positioned relatively nearer to a front waist region of the article than the third arm or the third arm may be positioned closer to a front waist region of the article than the first and second arms. The first and second pieces may include extension portions, which are positioned together when arranged in the absorbent article so as to define a closed perimeter together with the first and second arms of the Y-shape to form a substantially closed sided opening through the stiffening element. Alternatively, third and fourth arms of the X-shape define a space between them providing a second collapse prone portion of the absorbent article that may be centered on a central longitudinal axis of the absorbent article. The second collapse prone portion may, like the first collapse prone portion, be closed by extension portions of the third and fourth arms. The X-shape of the element thus allows first and second collapse prone portions to be defined that work together to enhance wearer comfort and article positioning relative to the wearer.

A longitudinal boundary between the first and second pieces of the stiffening element may function as a fold line to define a collapsible portion for providing a desired shape to the absorbent article when it is worn.

The present disclosure is also directed to an absorbent article comprising the element defining the shape. More particularly, the present disclosure provides an absorbent article that includes an element defining a shape that is more conveniently manufactured. As described above, there are a number of applications in absorbent articles where it is desirable to provide a fastening element or a stiffening element defining a complex shape.

More particularly, the present disclosure provides an absorbent article comprising a fastening element for fastening the absorbent article, preferably to underpants, or a stiffening element for providing a relatively stiff region of the absorbent article and for defining a collapse prone portion of the absorbent article to shape the absorbent article as desired, wherein the element defines a shape and comprises a first piece of planar material defining a bend when viewed in plan and a second piece of planar material defining a bend when viewed in plan, wherein the pieces are arranged together so that they together define the shape of the element. In other words, the pieces may be arranged so that an outside of the bends are in facing relation for the pieces to together define the shape of the element, such as a Y-, X-, m- or T shape of the element. Alternatively, the pieces may be arranged so that an outside of the bends face in opposing directions to thereby define a closed space shape, such as a four sided polygonal shape.

By placing the bend of the first piece and the bend of the second piece in facing relation so that the bends point in opposite directions, a Y-, m, T or X-shape is formed in a more material efficient manner as compared to if the shape was formed of a single piece. The pieces are better suited to be made from nesting pieces. This allows the shape to be made in a way that reduces waste material.

Preferably, the first and second pieces are cut from a web of fastening element or stiffening element material. The cut lines provide the first and second pieces of material with at least one bend in a path from one end of the piece to an opposing end.

Preferably, the first and second pieces define a generally V- or U-shape so that each of the first and second pieces has first and second legs. In one preferred embodiment, the first legs together define a first arm of the Y, m or T shape of the element, and the second legs respectively define second and third arms of the Y-, m- or T-shape of the element. Alternatively, the first and second legs of one of the V- or U-shapes provide first and second arms of the X-shape of the element and the first and second legs provide third and fourth arms of the X-shape of the element. Preferably, the V or U shape of the first piece is the same size and shape in plan as the V or U shape of the second piece. The first and second pieces could, however, be of different thickness. The first and second pieces can in their entirety define a V- or U-shape or the V-or U-shape may make up a portion of the first and second pieces. Likewise, the shape makes up at least a portion (i.e. a portion or the entirety) of the overall shape of the element.

Preferably, the first and second planar pieces of material are of the same size and shape when viewed in plan, yet rotated or flipped relative to one another so that the bends face one another rather than facing in the same direction. This will further simplify manufacture as the pieces are the same and thus can be continuously cut and applied to the absorbent article.

Preferably, the Y- or X-shape of the element is elongate (longest in one direction and shorter in a cross direction thereof) and the element is orientated longitudinally so that arms of the Y- or X-shape extend in opposing lateral directions and are disposed toward a waist region of the absorbent article. In terms of the fastening element, this provides good coverage of the article, in that more corner orientated portions are fastened by the arms, while a narrower, at least in use, crotch portion has an appropriately tailored fastening element shape. In the case of an element defining a Y-shape, a first arm of the Y shape extends substantially along a central longitudinal line of the absorbent article and is disposed toward a crotch portion of the absorbent article.

Preferably, the element is a fastening element, wherein a first arm of a Y-shape of the element extends to a relatively narrow crotch portion of the absorbent article, and the second and third arms extend to opposed corner portions of a relatively wide waist portion of the absorbent article. In the case of a stiffening element, the arms may also be orientated more toward a waist region (front or rear) and the other arm may be orientated more towards a crotch region, which can provide a comfortable absorbent article.

Also preferably, the fastening element is a hook type fastener, preferably for hooking to fabric of underpants or an adhesive type fastener for adhering to underpants.

Preferably, the element is a stiffening element, wherein first and second arms of the Y- or X-shape of the element define a relatively collapse prone portion of the absorbent article between the arms as a result of a region of the absorbent article between the arms being less stiff than a region of the absorbent article covered by the arms of the stiffening element. Likewise, third and fourth arms of the X-shape of the element define a further collapse prone portion of the absorbent article between the third and fourth arms as a result of a region of the absorbent article between the third and fourth arms being less stiff than a region of the absorbent article layered with the third and fourth arms.

The first and second pieces are preferably formed so that they are generally elongate and are cut to have inside and outside (with respect to the bend) opposed lateral edges. The inside and outside edges are the same in length and shape, yet laterally spaced apart from one another to define a width of the pieces. This allows them to be cut in a convenient manner in terms of manufacturing by utilizing the same blade to cut both edges.

A shape of the pieces can be determined from a central line between first and second opposed lateral edges of the pieces, wherein the pieces are elongate. If the central line deviates from a straight line, then a bend is provided in the piece. The point at which the central line deviates from a straight line defines the beginning of a bend. The pieces will either bend left or right of the central line. The first and second pieces may be brought together so that a left bend is arranged adjacent to a right bend to define the shape.

The first and second pieces are preferably arranged in the absorbent article about a line of symmetry, which is preferably arranged longitudinally with respect to the absorbent article (with respect to a use direction from front waste region to crotch region and optionally to rear waist region) and is preferably positioned along a central longitudinal line of the absorbent article such that the first and second pieces are mirror images of one another about the line of symmetry.

The first and second pieces can be described as following a curved, curvilinear or linear path having a local maxima at the bend. Respective maxima points of the first and second pieces are brought into substantial contacting relation to define the Y-, m-, X- or T shaped fastening element.

The absorbent article of the method or apparatus aspects of the present disclosure may be described as having an absorbent core captured between a bodyside layer and an outer cover layer. The bodyside layer is liquid permeable to allow urinal or menstrual discharge through to the absorbent core. The outer cover layer is generally liquid impermeable to stop urinal or menstrual discharge soiling an underpant. The absorbent core is provided to absorb urinal or menstrual discharge.

BRIEF DESCRIPTION OF THE FIGURES

FIG. 2 shows the absorbent article of FIG. 1 in a curved, use configuration for conforming to the body of a user.

FIG. 8a illustrates a cutting pattern for making curved v-shaped pieces. FIG. 8b illustrates an element defining an m-shape that is made from the pieces made by the cutting pattern of FIG. 8a.

FIG. 9a illustrates a cutting pattern for making straight edged v-shaped pieces. FIG. 9b illustrates an element defining a diamond shape that is made from the pieces made by the cutting patter of FIG. 9a.

DETAILED DESCRIPTION OF PREFERRED EMBODIMENTS OF THE INVENTION

Figure 1:
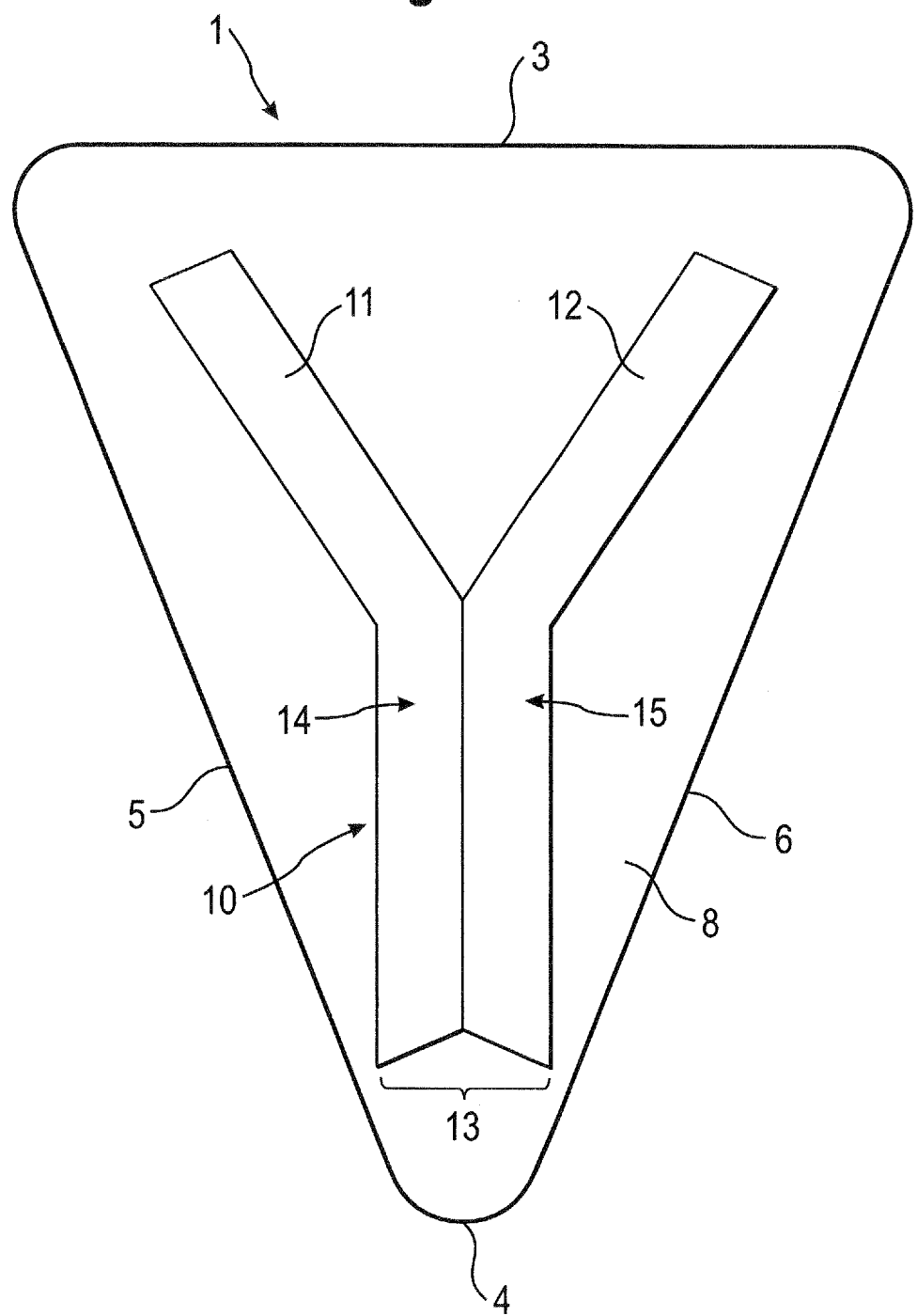
FIG. 1 shows an absorbent article for men having a Y-shaped fastener on an outer cover for securing the article to underpants. The absorbent article is shown in a flattened configuration.

FIG. 1 shows a male adult incontinence absorbent article 1 according to an embodiment of the present invention. The absorbent article 1 is generally triangularly shaped when laid out flat, as shown. FIG. 2 shows the same male adult incontinence absorbent article 1 in a condition whereby elastics 2 have shaped the article 1 so as to conform to the genitalia of the male adult wearer. Referring back to FIG. 1 and/or 2, the article 1 has a waist end 3 for being positioned toward a waist of a wearer and a crotch end 4 that is to be positioned at a crotch region of a wearer, beyond the genitalia of the wearer. Two corners of a triangle defining the general shape of the absorbent article 1 are provided at opposing sides of the waist end 3, while the crotch end 4 provides a third corner. Opposing sides edges 5, 6 connect the waist end 3 to the crotch end 4 and taper toward one another from the waist end 3 to the crotch end 4 to accommodate legs of the wearer. The elastics 2 are such that the crotch end 4 is pulled toward a longitudinal (from waist end 3 to crotch end 4) centre of the article 1, while the opposing sides 5,6 are pulled toward a lateral centre of the article 1 in order to form a bowl shape for cupping the male genitalia (including penis and scrotum). The bowl shape is designed to avoid leaking of urine from opposing sides 5, 6 and the crotch end 4 of the absorbent article 1, without requiring the absorbent article to extend to a buttock side waist region of the wearer.

The absorbent article 1 comprises a liquid permeable layer 7 to be positioned against a body of a wearer and to allow urine to pass to an underlying absorbent core (not shown). A liquid impermeable layer 8 is for positioning against underpants of a wearer and is arranged to prevent urine from passing from the absorbent core to the underpants. The absorbent core may comprise cellulose fluff fibers and superabsorbent polymers and desirably in an amount able to absorb a typical urination of the incontinent wearer. The liquid permeable layer 7 may be made of a non-woven material or perforated plastic. The liquid impermeable layer 8 may be made of polyethylene or polypropylene plastic.

The absorbent article 1 is to be provided with means for attaching it to underlying underpants of a wearer. Accordingly, the outer cover 8 includes a fastener 10 that is removably attachable, with minimal abrasion on removal, to the underpants. Thus, the fastener 10 faces the underpants when the article 1 is worn with the bodyside layer 7 positioned against a wearer.

Male incontinence absorbent articles of the type described above, or similar thereto, are known in the art. Reference is made to prior disclosures such as U.S. Pat. No. 5,486,186 and PCT patent publications WO 86/06620, and WO 2004/019850, for example, for further information on this known type of male incontinence absorbent article.

In the absorbent article 1 of FIG. 1, the means for attaching to an underpant is a generally Y-shaped fastening element 10 made of two pieces of fastening element material. The Y-shaped fastening element 10 has first and second arms 11, 12 extending from a third arm 13. The third arm 13 is centred on a line of bisection of the first and second arms 11, 12. A first piece of fastening element material 14 provides one lateral half of the Y-shaped fastening element 10 and a second piece of fastening element material 15 provides the other lateral half of the Y-shaped fastening element 10. The lateral halves can be understood in the sense of opposing sides of the line of bisection of the first and second arms 11, 12. That is, the first piece of fastening element material 14 provides the first arm 11 of the Y-shaped fastening element 10 and one lateral half of the third arm 13 and the second piece of fastening element material 15 provides the second arm 12 of the Y-shaped fastening element 10 and the other lateral half of the third arm 13.

The Y-shaped fastening element 10 is arranged so that the first arm 11 extends to a first corner portion of the absorbent article 1, the second arm 12 extends to a second corner portion and the third arm 13 extends to a third corner portion. Thus, all three corner portions of the generally triangular shaped absorbent article 1 are able to be fastened to the underpant.

The pieces of fastening element material 14, 15 are hook-type fastening material that hook-in to the underlying underpant's fabric. The hooks are particularly fine so as to be low in abrasiveness, yet sufficiently plentiful as to securely fasten to the fabric of underpants.

The absorbent article 1 can be manufactured as shown in FIG. 3. A web of fastening element material 16 (FIG. 3(a)) is cut into successive pieces of fastening element material 17 according to the cut pattern shown. Two successive pieces provide the first and second pieces of fastening element material 14, 15 described above (FIG. 3(b)).

Figure 3A:
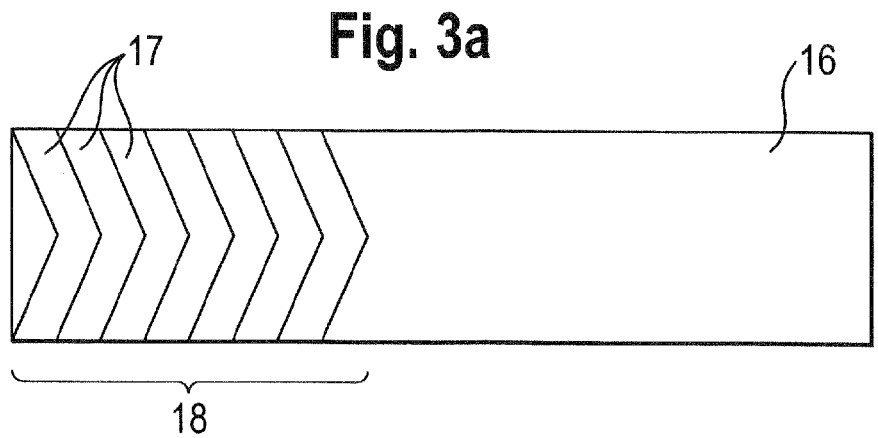
FIG. 3 illustrates steps of manufacturing the Y-shaped fastener of the absorbent article of FIGS. 1 and 2 from two pieces of fastener material cut from web fastener material and oriented to together form the Y-shape.
Figure 3B:
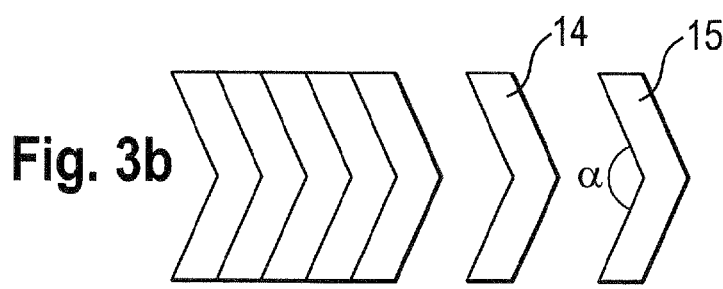

The cutting pattern 18 provides successive pieces of v-shaped material, where the v-shape defines a wide angle between first and second arms of the v-shape. That is, first and second arms of the v-shape may have an angle α (FIG. 3b)

between them that is between 100° and 170°, and preferably between 100° and 160° in order to provide proper spacing between arms 11, 12 of the Y-shaped fastening element 10. The cutting pattern 18 is made up of successive incisions through the web 16 that are themselves v-shaped. Each incision is longitudinally spaced along the web 16 to make first and second pieces of fastening element material 14, 15 by three such incisions. Each incision extends from one lateral side of the web of fastening element material 16 to the opposing lateral side thereof. The cutting pattern 18 is such that there is 0% wastage of fastening element material (no trimmings) once the cutting run is up and running (referring to FIG. 3(a), there is a waste piece because of the linear leading edge of the web of fastening element material 16).

Figure 3C:
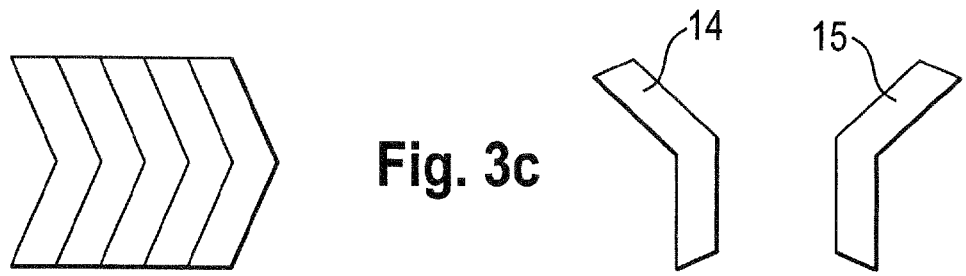
Figure 3D:
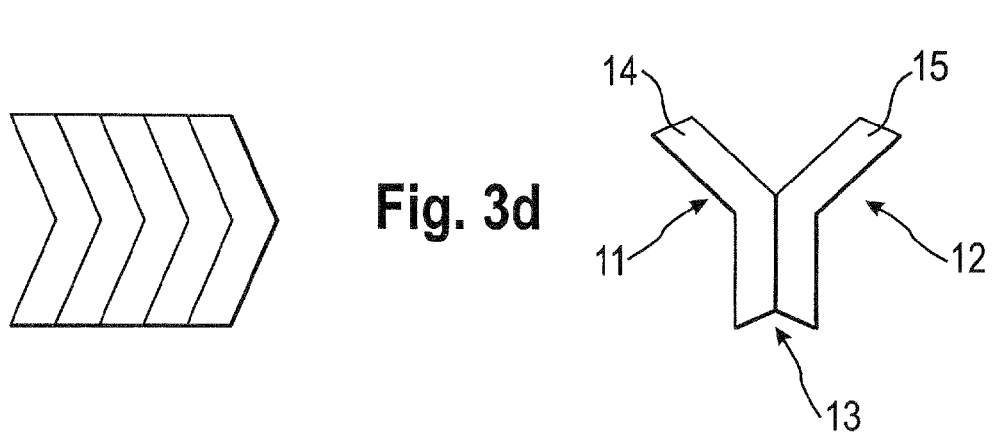

Referring back to FIG. 3(a), the first and second v-shaped planar pieces 14, 15 define a bend, when viewed in plan, between the arms of the v as opposed to a linear or straight piece. The first and second pieces 14, 15 are rotated as shown in FIG. 3(c) so that the respective bends face one another. That is, if the side of the bend defining an angle α between opposing legs of the bend of less than 180° is considered an inside edge and the side of the bend defining an angle between opposing legs of the bend of greater than 180° is considered an outside edge then the first and second pieces of fastening element material 14, 15 are relatively rotated so that their outside edges face one another and their inside edges face away from one another (FIG. 3(c)). The first and second pieces of fastening element material 14, 15 are brought into substantial contacting relation (FIG. 3(d)) in that one side of an outside edge of each piece is brought substantially into touch, thereby defining the third arm 13 of the Y-shaped fastening element 10. The other side of the outside edge of the pieces 14, 15 extend away from one another to define the first and second arms 11, 12 of the Y-shaped fastening element 10. The point of the v-shape of the first and second pieces 14, 15 is brought together to define an intersecting point of the three arms of the Y-shaped fastening element 10.

The Y-shaped fastening element 10 so formed is applied to an outer cover 8 of an absorbent article 1 with the underpant adhering, e.g. hook, surface of the fastening element 10 facing outwardly. The fastening element 10 may be applied to an outer cover web that is subsequently formed into part of an absorbent article, i.e. absorbent article precursor material, or it can be applied to an outer cover layer of a web of a body side liner, absorbent core and outer cover that is subsequently cut into respective absorbent articles 1. Alternatively, the absorbent article 1 may be preformed and the Y-shaped fastening element 10 can be attached to the outer cover 8.

Figure 4:
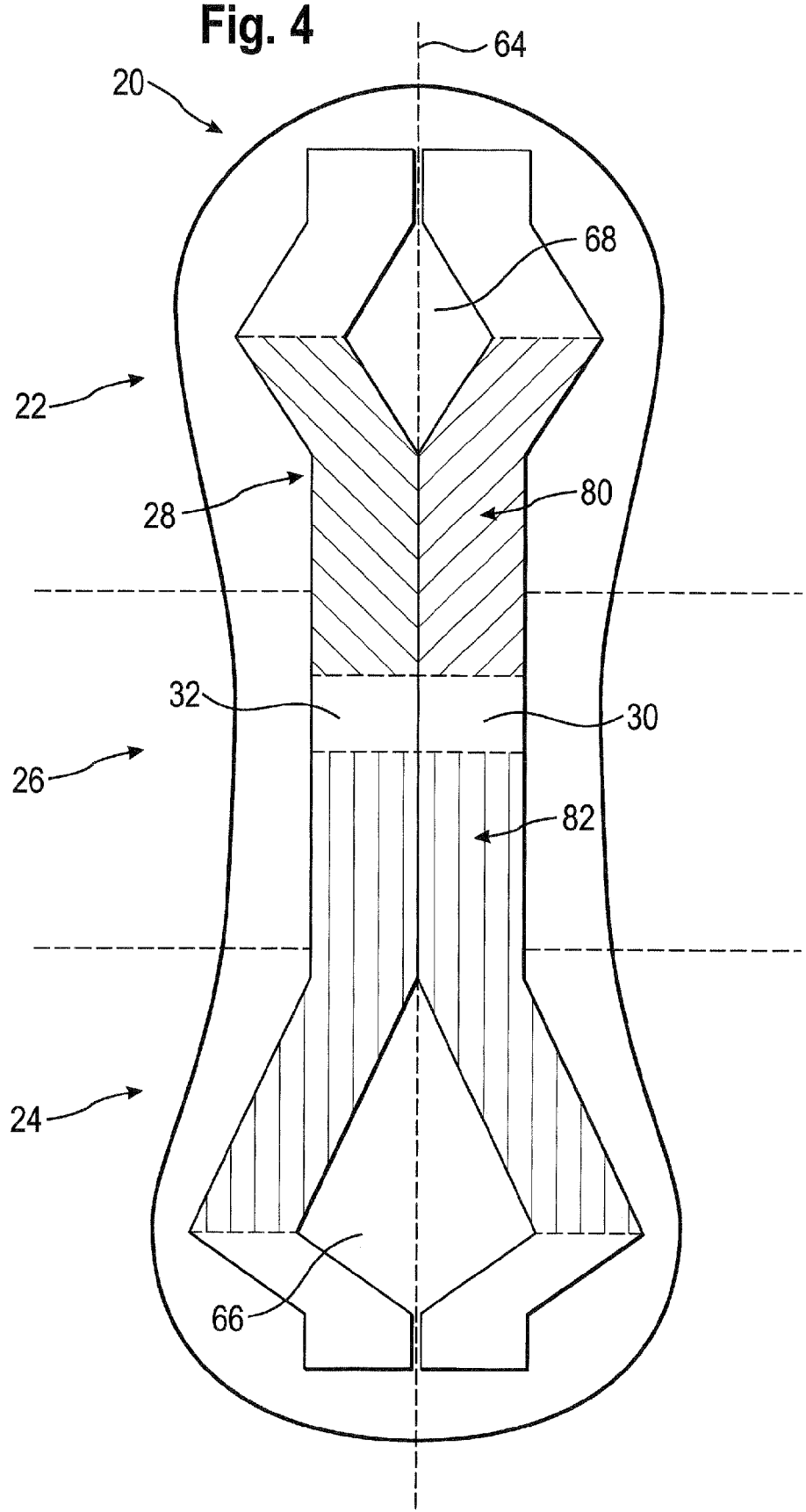
FIG. 4 illustrates a feminine absorbent article having a stiffening element formed from two pieces of stiffening material together defining front and back collapse prone portions.

In another embodiment as shown in FIG. 4, there is provided a feminine absorbent article 20 having a front portion 22 for placement at a front crotch side of a wearer, a rear portion 24 for placement at a rear crotch side of a wearer and an intermediate crotch portion 26 that is narrow relative to the front and rear portions 22, 24 for accommodating legs of a wearer. The absorbent article 20 defines a general hour glass shape in plan view, as shown. The absorbent article can be a sanitary towel for absorbing menstrual discharge or an incontinence towel for absorbing urinal discharge.

The absorbent article 20 comprises a bodyside layer that is liquid permeable for passing liquid discharge into the absorbent article 20. The absorbent article 20 further comprises an absorbent layer, which is able to absorb an amount of urinary or menstrual discharge expected for the type of absorbent article 20. An outer cover is further included and the absorbent layer is placed between the outer cover and the bodyside liner. The outer cover is liquid impermeable for avoiding bodily fluids penetrating the absorbent article 20 and reaching an underlying underpant. The bodyside liner and the outer cover are bonded together about a periphery of the absorbent layer to capture the absorbent layer between them.

The absorbent article 20 comprises a stiffening element 28 that is made of two pieces of stiffening element material 30, 32. The stiffening element 28 may be made by the absorbent layer, or it can be a further element of the absorbent article 20 such as a plastic or paper layer. The stiffening element 28 provides a relatively stiff region of the absorbent article 20 where it is layered as compared to other regions of the absorbent article where the stiffening element 28 is not located.

Figure 5:
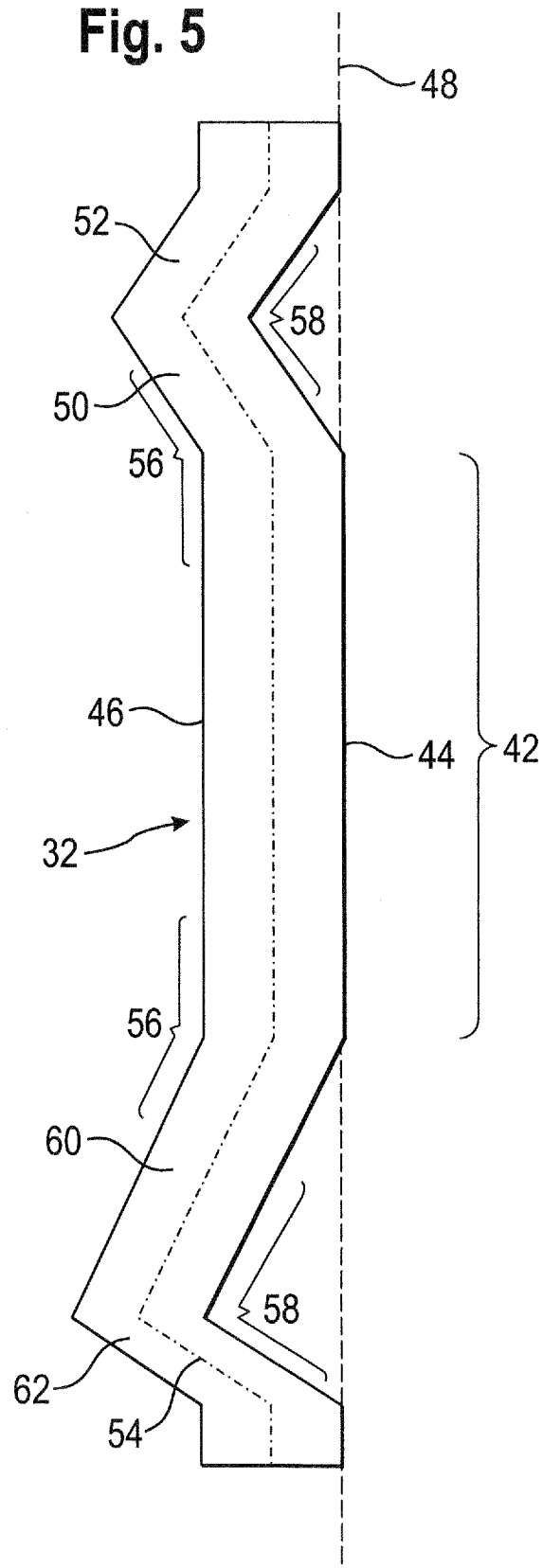
FIG. 5 illustrates a first piece of the stiffening element of the absorbent article of FIG. 4. The first piece is to be combined with a second piece that is the same size and shape as the first piece to together form the stiffening element.

Referring to FIGS. 4 and 5, a first stiffening element piece 30 is shown. The first stiffening element piece 30 is to be combined with a second stiffening element piece 32 as shown in FIGS. 4 and 5 in order to together define the stiffening element 28. Referring to FIG. 5, the second stiffening element material piece 32 has a centrally located, in the longitudinal direction, straight portion 42 having opposed lateral edges 44, 46 that run parallel to one another. A shape of the piece 30 can be defined by a line 54 passing centrally through the opposed lateral edges 44, 46. An inside lateral edge of the straight portion 42 runs along a longitudinal line 48. Thus, following the laterally central line of the piece 30 from the central straight portion 42 toward opposing ends, the piece 30 has first bends 50, 60 at opposed ends of the straight portion 42 so that the piece 30 extends outwardly from the longitudinal line 48 and then has second bends 52, 62 from the path of the first bend 50 so that the piece extends back inwardly to meet the longitudinal line 48. These outward and inward bends 50, 52, 60, 62 define first and second v-shapes 56, 58 at opposing longitudinal ends of the piece 30, wherein the open side of the second v-shape 58 faces the longitudinal line 48 and the open side of the first v-shape faces away from the longitudinal central line 48. One of the second v-shapes 58 is more elongate than the other v-shape 58 at an opposed longitudinal end of the second piece 32. Further, the more elongate of the v-shapes 58 has one leg formed by a first bend 62 adjacent the straight portion 42 that is more steeply angled relative to the longitudinal line 48 than the bend 60 forming the other leg of the more elongate v-shape 58.

The first piece of stiffening element material 30 is of the same shape and size, in plan, as the second piece of stiffening element material 30.

The first and second stiffening pieces of stiffening element material 30, 32 are arranged on either side of a central longitudinal line 64 that runs through a lateral centre of the absorbent article 20 to together form a stiffening element 28 of the absorbent article 20. The first and second pieces of stiffening element 30, 32 are arranged on the absorbent article 20 so that inside edges 44 of their respective straight portions 42 are brought into contacting relationship. Further, the v-shapes 56, 58 at opposing ends of respective first and second pieces 30, 32 are longitudinally aligned so as to form a front diamond shaped opening 68 in the stiffening element at a front end 22 of the absorbent article 20 and to form a rear diamond shaped opening 66 at a rear end 24 of the absorbent article 20. The rear diamond shaped opening 66 is more elongate than the front diamond shaped opening 68 as a result of the more elongate of the second v-shapes 58 of the first and second pieces 30, 32 being longitudinally aligned and brought laterally together.

As can be seen from the line shading of FIG. 4, the stiffening element 28 defines two y-shaped portions 80, 82, one of which has the arms of the Y-shape 80 extending in the front region 22 of the absorbent article and a third arm that extends in the crotch region 26 of the absorbent article 20 and the other of which is oppositely oriented such that first and second arms of the Y-shape 82 are extending in the rear region 24 of the absorbent article 20 and the third arm extends in the crotch region 26 thereof. Each Y-shaped portion 80, 82 of the stiffening element 28 is formed so that a first arm and one lateral half of the third arm is provided by one of the pieces of stiffening element material 30, 32 and a second arm and the other half of the third arm is provided by the other of the pieces of stiffening element material 30, 32.

The stiffening element 28 is relatively stiff at a region of the absorbent article where it lays as compared to other portions of the absorbent article 20 where the stiffening element 28 does not lay. The front opening 68 of the stiffening element 28 of the absorbent article 20 defines a front collapse prone portion 68 of the absorbent article 20. The front collapse prone portion 68 is designed to collapse when the article 20 is squeezed between legs of a wearer to shape the article 20 so that it curves upwards towards the crotch of the wearer and provides a more cup-like, receptacle shape for the absorbent article 20. The rear collapse prone portion 66 of the stiffening element 28 is designed to collapse when worn as a result of the article being squeezed between the legs so to form a longitudinal ridge for placement between buttocks of a wearer so as to laterally secure a position of the absorbent article 20 when worn. Optionally, the absorbent article 20 comprises just one of the front and rear collapse prone portions 66, 68.

Figure 6:
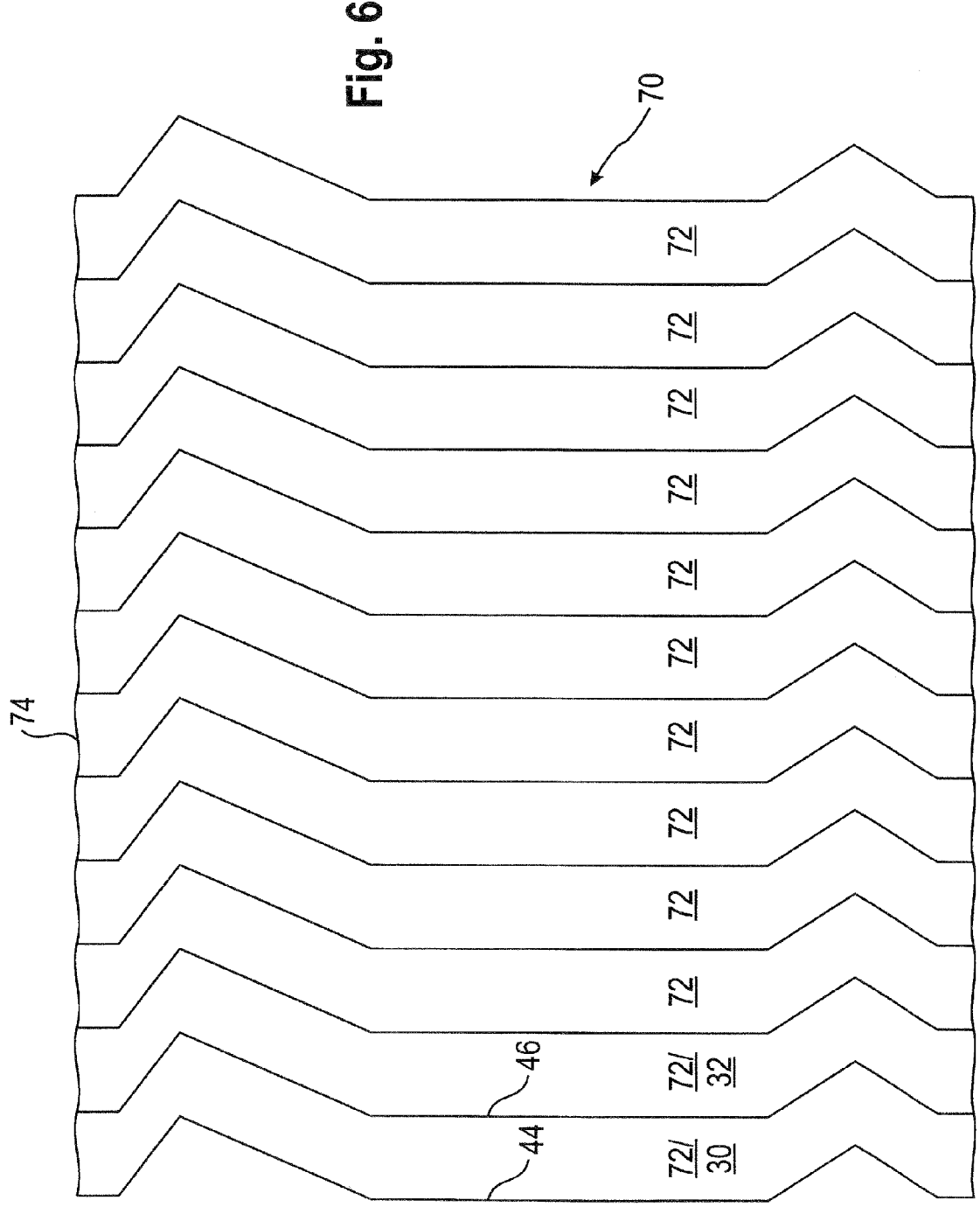
FIG. 6 illustrates a cutting pattern for a web of material for forming a number of the stiffening element pieces as shown in FIG. 5.

FIG. 6 shows a web of stiffening element material 74 that may be an absorbent layer, a web of paper or a web of plastic or any other material that is able to provide a relatively stiff portion of an absorbent article 20. A cutting pattern 70 is illustrated on the web 74, which shows where the web 74 will be cut as it is fed through a cutting apparatus so as to successively form separated pieces of stiffening element material 72.

In a method of manufacture of the absorbent article 20 of FIGS. 4 and 5, a web of stiffening element material 74 is fed continuously to a cutting apparatus such as a rotating cylindrical drum having a suitably shaped blade for forming opposed edges 44, 46 of each piece of stiffening element material 72. The drum is rotated at such a speed that the blade is able to cut each opposed lateral edge 44, 46 of the pieces 72. One of every two pieces 72 is flipped relative one other of the two pieces 72 to form the first and second pieces of stiffening element material 30, 32. The first and second pieces 30, 32 are applied to a web of absorbent article material such as a bodyside liner, an outer cover, an absorbent core or an assembly thereof or the first and second pieces are applied to a feed of preformed absorbent articles. In the case of the stiffening element pieces 30, 32 being made of an absorbent layer of the absorbent article material, they are laid on a web of outer cover material or bodyside liner material. The first and second pieces 30, 32 are applied so that the pieces are longitudinally aligned on the absorbent article and laterally brought together at the central longitudinal line 64 of the absorbent article 20.

The first and second pieces of stiffening element material 30, 32 are arranged on the absorbent article such that they are symmetrical about the central longitudinal line 64 of the absorbent article 20 as shown in FIG. 4. The pieces 30, 32 of stiffening element material 30, 32 are not symmetrical about a central lateral line of the pieces and thus can not be rotated relative to one another without flipping during manufacture as this would bring the different length v-shapes 56, 58 into correspondence. By flipping one of the pieces 30, 32 relative to the other, the same shape v-shapes 56, 58 of the respective pieces 30, 32 can be brought into lateral correspondence to form the front and rear diamonds 66, 68 as required. In the embodiment of FIGS. 1 to 3, the fastening element material pieces 14, 15 have a central, laterally extending line of symmetry and thus can be rotated relative to one another without flipping to form the fastening element 10. Further embodiments of the invention are disclosed in FIGS. 7 to 9.

Figure 7:
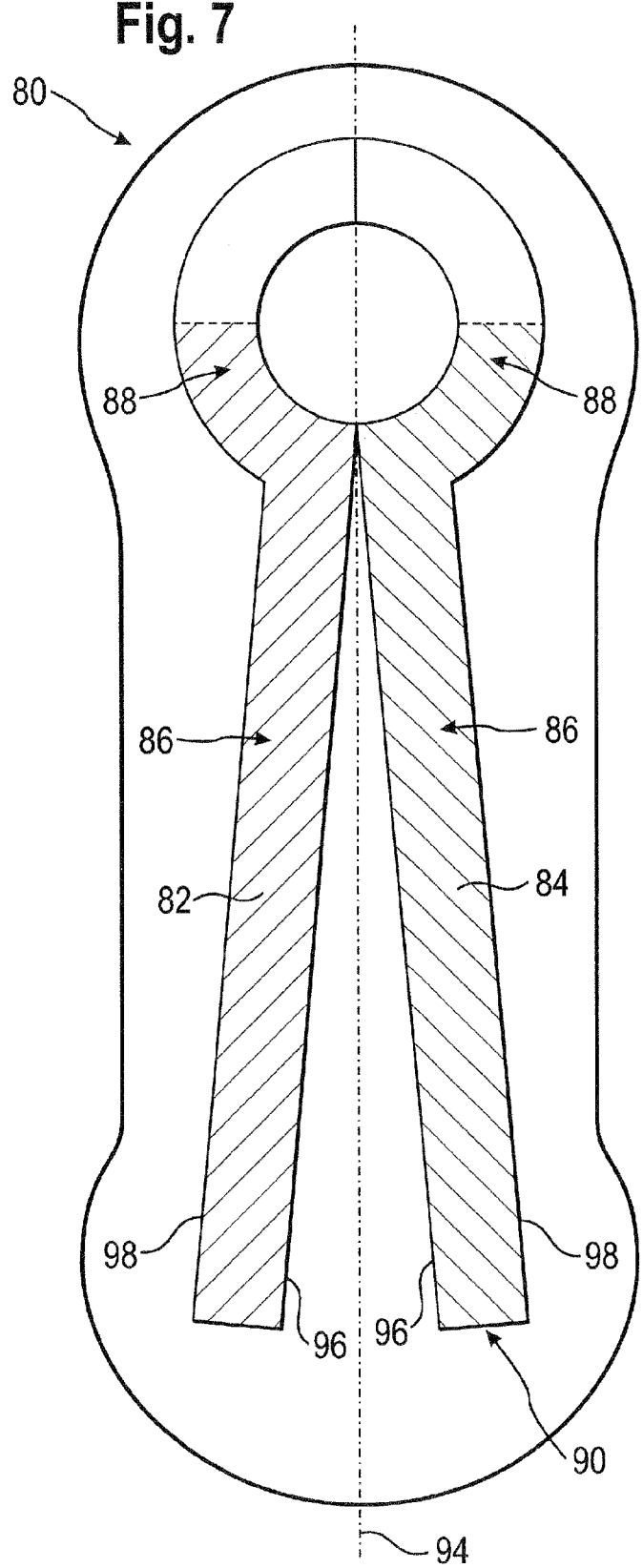
FIG. 7 illustrates a panty liner having a stiffening element defining an X-shape using first and second pieces.

In FIG. 7, there is disclosed an absorbent article 80 in the form of an hour-glass shaped absorbent panty-liner. The absorbent article 80 is substantially as described above with respect to FIGS. 4 to 6. There are shown first and second pieces 82, 84 of stiffening element material. The pieces 82, 84 are planar pieces and each define a straight portion 86 and a bow shaped portion 88, when viewed in plan, at one end of the straight portion 86. The pieces 82, 84 are brought together so as to together define a desired shape of a stiffening element 90. The bow shaped portions 88 of the first and second pieces 82, 84 are brought together so that they together form a circle, with each bow shaped portion 88 defining half of the circle. The straight portions 86 are brought together in a way such that they are more gradually spaced apart from the end of the straight portions 88 having the bow shaped portion 88 thereat (where they are substantially contacting) to the other end of the straight portions 86. The first and second pieces 82, 84 are substantially longitudinally aligned and are mirror images of one another about a central longitudinal line 94. The desired shape can be seen as including an X-shape in plan in that there is a point of intersection where the pieces 82, 84 are in substantial contact and four arms extending away from the point of intersection, as illustrated by the shaded area of the stiffening element 90.

The hollow in the circular head of the stiffening element 90 as defined within the bow shaped portions 88 offers a collapse prone portion, as does the expanding space between the straight portions 86. These collapse prone portions aid user comfort and positioning of the absorbent article 80 when it is worn. The circular head portion is positioned in a front of the panty liner 80, while the most spaced apart part of the straight portions 82, 84 is positioned in a rear portion of the panty liner 80.

To manufacture, separate blade shapes will be needed to define opposing lateral sides 96, 98 of the pieces of stiffening element material 82, 84. An inside edge (with respect to the bend defined by the bow shaped portions 88) of the pieces 82, 84 matches an outside edge 98 of the pieces 82, 84 except for the bow shaped portions 88. Therefore, a different blade is required of reach edge 96, 98 of the first and second pieces 82, 84. A cutting drum could, therefore be provided with first and second different blades, or there could be first and second cutting drums with respective different blades.

A consequence of the differing shaped outside edges 96 to the inside edges 96 is that the outside edge 98 of the bow shaped portion 88 of the second piece 84 only partially mates with the inside edge 96 of the bow shaped portion 88 of the first piece 82. Nonetheless, forming the stiffening element 90 of first and second pieces 82, 84 still allows trimmings to be reduced as compared to stamping the stiffening element 90 as one piece because of the partial mating, which allows partial nesting, of the first and second pieces 82, 84.

FIG. 8a discloses a cutting pattern whereby curved v shaped cut lines 101 are regularly longitudinally spaced apart along the elongate web 100. The cutting pattern serves to make a stream of planar pieces, including first and second pieces 102, 104, that are v-shaped when viewed in plan, where the v-shape is curved in defining an inside edge 106 and an outside edge 108 thereof, as shown in FIG. 8b. The first and second pieces 102, 104 are positioned on an absorbent article in side by side relation and longitudinally aligned relation. The pieces 102, 104 are rotated toward one another so that the outside edges 108 are brought into substantial contacting relation. The outside edges are brought together so that the first and second pieces 102, 104 together define a substantially m-shaped element 110 when viewed in plan, as shown in FIG. 8b. The m-shaped element is a useful configuration for a stiffening element or a fastening element of an absorbent article. Since the inside edge of the bend of the second piece 108 mates completely with the outside edge of the bend of the first piece, an m-shaped element 110 can be created without material waste in cutting the web 100.

FIG. 9a discloses a cutting pattern whereby v-shaped cut lines 122 are regularly longitudinally spaced apart along the longitudinal direction of the elongate web 120. The cut lines 122 are made up of two straight lines coming together at a point. A stream of v shaped planar pieces is thus produced, which includes first and second pieces 124, 126 as shown in FIG. 9b. The first and second pieces 124, 126 are rotated (by 180°) relative to one another, which in this case may be best done by flipping one of the pieces 124, 126 relative to the other of the pieces 124, 126, so that the inside edges 128 face one another and the outside edges 130 face away from one another to thereby define a diamond shaped element 140 when viewed in plan. The diamond shaped element 140 is envisaged to be another useful configuration for a stiffening element or a fastening element. Again, because the same cutting line is used to define edges of adjacent pieces 124, 126 of the fastening element material, they are substantially perfectly nested to substantially eliminate waste trimmings.

In the embodiments of FIGS. 8 and 9, the first and second pieces do not actually come into contact with one another. Machine tolerances may mean that there may be a gap between the first and second pieces of, it is expected, about 2 mm. Such a gap, or even up to about 5 mm, would not prevent the pieces as together defining a shape of the fastening or stiffening element.

A number of modifications could be made to the preferred embodiments given above, some examples of which are outlined below.

The hook type fastening element 10 of the absorbent article 1 of FIGS. 1 to 3, could instead be a peelable adhesive fastening element or any other known fastening element material that can be fed as a continuous web. If the fastening element 10 is a peelable adhesive element, then the continuous web may comprise a substrate, a releasable liner and an adhesive layer therebetween. The user peels the releasable liner from the substrate to expose the adhesive layer in order to secure the absorbent article 10 to an underlying pant.

The absorbent article 1 of FIGS. 1 to 3 may instead or in addition of comprising a y-shaped fastening element comprise a y-shaped stiffening element. The stiffening element may be made by the absorbent layer, or it can be a further element of the absorbent article such as a plastic or paper layer. The stiffening element provides a relatively stiff region of the absorbent article where it is layered as compared to other regions of the absorbent article where the stiffening element is not located. Shapes other than a y-shape are envisaged for providing a fastening element or stiffening element in an embodiment of the invention. For example, first and second pieces 14, 15 as shown in the embodiment of FIGS. 1 to 3 could be oriented relative to one another so as define an x-shape, whereby the bends of each piece 14, 15 are brought into lateral and longitudinal alignment and oriented so that they point toward one another to provide a central intersection point of the x-shape and further whereby the first and second legs of each of the v-shaped pieces 14, 15 respectively provide one of the four legs of the x-shape. This may be particularly advantageous in the case of a fastening element for an hour glass shaped absorbent article such as the article 20 shown in FIGS. 4 and 5 since each of the legs of the x-shaped fastening element can extend to an opposite corner portion of absorbent article to secure all four corner portions of the hour glass shaped absorbent article to an underlying pant. This will help avoid corners of the absorbent article coming away from the pant and folding over themselves.

In the embodiments of the invention shown in FIGS. 1 to 6, the base leg of the y-shaped element is twice as wide laterally as the arms thereof. The cutting pattern could be adjusted so that the base leg is the same thickness as the arms for aesthehetic purposes. This would, however, involve waste trimmings and complexity being introduced into the web cutting and piece arranging process.

In the preferred embodiments described above with respect to FIGS. 1 to 9, the first and second pieces of fastening or stiffening element are cut from the same web. The first and second pieces are then rotated (flipped or rotated in plane) relative to one another to form a stiffening or fastening element defining a Y, T, X, m or diamond shape. It may prove advantageous for manufacturing reasons to feed a first web of material for providing the first pieces and a second web of material for providing the second pieces. There may be separate cutting stations for each web of material. The first web of material is cut into successive pieces as the first pieces of element material and the second web of material is cut into successive pieces of the second pieces of element material. The cutting patterns for each web and the feed direction of each web could be arranged so that relative rotation of the first and second pieces is not necessary since they would be cut and fed in an orientation that allows them to be applied to a preformed absorbent article or precursor absorbent article web material in that orientation and still form the Y, T, X, m or diamond-shape.

If the two pieces are cut from two webs the stiffening element 28 of FIGS. 4 to 7 could instead be a fastening element, such as a hook type fastening element or an adhesive type fastening element that is applied to an underside of an outer cover of the absorbent article 20. The pieces from one of the webs can then be cut in a shape that are inverted in relation to the shape of the pieces from other web. Thus the pieces does not have to flipped and the elements in FIG. 4-7 can also be made from two-sided materials.

In the embodiment described above with respect to FIGS. 1 to 9, the inner and outer lateral edges of the pieces are made up of straight lines angled relative to one another. The cut edges of the pieces could, however, include curved lines. That is, the pieces could follow a continuously curved path or a curvilinear path made up of curved and straight portions. Thus, the v-shaped pieces 14, 15 of the embodiment of FIGS. 1 to 3 could be u-shaped, which would define a more curved, perhaps more aesthetically pleasing, fastening element. Likewise, the pieces 30, 32 of stiffening element material of FIGS. 4 to 6 could be curvilinear so as to define more rounded openings 66, 68 than the diamond shaped ones shown.

In the embodiments of FIGS. 1 to 9, the pieces of stiffening or fastening element material are brought into contact with one another. They could, however, partially overlap or have a small gap between them (small enough that the y-shape is still identifiable and they still operate together to perform the fastening or stiffening function). Preferably, however, there is no overlap of the pieces since this is a waste of material at the overlap area comparable to waste trimmings at the cutting stage. It is also preferred for aesthetic and functional reasons for the pieces to be in contact, preferably along a central longitudinal line of the absorbent article.

The invention claimed is:

1. A method of manufacturing an absorbent article comprising an element applied thereto that defines a shape, the method comprising:
providing first and second planar pieces of material that define a bend, when viewed in plan view,
applying the first and second planar pieces so as to be arranged together on the absorbent article such that the first and second planar pieces of material and their respective bends together define the shape of the element,
wherein the first piece of material is arranged on the absorbent article on a first side of a line of symmetry for the first and second pieces of material, and the second piece of material is arranged on the absorbent article in substantial contact with the first piece of material on a second side of the line of symmetry such that the first and second pieces of material form mirror images of one another.

2. The method of claim 1, wherein the first and second pieces of material define a general V shape or a general U shape, wherein an outside edge of the bend of the U or V shape or the bight of the U-shape or the point of the V-shape of the first piece is brought together with an outside edge of the bend of the U or V shape or the bight of the U-shape or the point of the V-shape of the second piece as the pieces are arranged on the absorbent article so that first legs of the U- or V-shape of the first and second pieces provide respective arms of the shape and either second legs of the V- or U-shapes of the first and second pieces together define a third arm of the shape or they respectively define third and fourth arms of the shape.

3. The method of claim 1, wherein the element is a fastening element and the fastening element is applied to the absorbent article so as to provide a fastener to fasten the absorbent article to underpants.

4. The method of claim 3, wherein the absorbent article has a narrowed crotch portion for location between the legs of a wearer and a wider waist portion for location nearer the waist of a wearer, and wherein first and second arms of the shape of the element extend respectively to opposed corner portions of the wider waist portion.

5. The method of claim 4, wherein the element defines the shape and a third arm of the shape of the element extends substantially along a longitudinal line of the absorbent article in the narrow crotch portion.

6. The method of claim 4, wherein the element defines the shape and a third arm of the shape of the element extends substantially along a central longitudinal line of the absorbent article in the narrow crotch portion.

7. The method of claim 1, wherein the element is a stiffening element providing a relatively stiff region to the absorbent article and defining a relatively collapse prone portion of the absorbent article so that when the absorbent article is worn, the article is shaped by the relatively collapse prone portion.

8. The method of claim 1, wherein the line of symmetry is arranged longitudinally with respect to the absorbent article.

9. The method of claim 1, wherein the line of symmetry is arranged as a central longitudinal line of the absorbent article.

10. A method of manufacturing an absorbent article comprising an element applied thereto that defines a shape, the method comprising:
providing first and second planar pieces of material that define a bend, when viewed in plan view,
applying the first and second planar pieces so as to be arranged together on the absorbent article such that the first and second planar pieces of material and their respective bends together define the shape of the element,
wherein the first and second pieces of material are arranged on the absorbent article on either side of a line of symmetry for the first and second pieces of material such that they form mirror images of one another,
further comprising cutting a web of material into the first and second pieces so that the bends are facing in the same direction and relatively rotating or relatively flipping the pieces of material so that the bends face in opposed directions as they are arranged on the absorbent article.

11. A method of manufacturing an absorbent article comprising an element applied thereto that defines a shape, the method comprising:
providing first and second planar pieces of material that define a bend, when viewed in plan view,
applying the first and second planar pieces so as to be arranged together on the absorbent article such that the first and second planar pieces of material and their respective bends together define the shape of the element,
wherein the first and second pieces of material are arranged on the absorbent article on either side of a line of symmetry for the first and second pieces of material such that they form mirror images of one another,
wherein at least one web of material is cut in a cut line across the at least one web into successive pieces so that a rearward edge of succeeding pieces defines a forward edge of preceding pieces, thereby providing the first and second pieces of material.

12. A method of manufacturing an absorbent article comprising an element applied thereto that defines a shape, the method comprising:
providing first and second planar pieces of material that define a bend, when viewed in plan view,
applying the first and second planar pieces so as to be arranged together on the absorbent article such that the first and second planar pieces of material and their respective bends together define the shape of the element,
wherein the first and second pieces of material are arranged on the absorbent article on either side of a line of symmetry for the first and second pieces of material such that they form mirror images of one another,
wherein at least one web is cut into successive pieces of material, thereby providing the first and second pieces, that nest with one another to such an extent that a ratio of area of waste trimmings to area of the at least one web is less than 0.3.

13. An absorbent article, comprising:
(1) a fastening element for fastening the absorbent article to underpants; or
(2) a stiffening element for providing a relatively stiff region of the absorbent article and for defining a collapse prone portion of the absorbent article to shape the absorbent article as desired;
the element defining a shape and comprising a first planar piece of material defining a bend, when viewed in plan view, and a second planar piece of material defining a bend, when viewed in plan view, wherein the first and second pieces of material are arranged together on the absorbent article and together define the shape of the element,
wherein the first piece of material is arranged on the absorbent article on a first side of a line of symmetry for the first and second pieces of material, and the second piece of material is arranged on the absorbent article in substantial contact with the first piece of material on a second side of the line of symmetry such that the first and second pieces of material form mirror images of one another.

14. The absorbent article of claim 13, wherein the first and second pieces of material are of the same size and shape, yet rotated or flipped relative to one another from a configuration wherein the first and second pieces are nestable with one another and the bends face in the same direction to a configuration wherein the bends face in opposed directions so that the first and second pieces cooperate to define the shape.

15. The absorbent article of claim 13, wherein the first and second pieces define a generally V- or U-shape so that each of the first and second pieces has first and second legs extending from a point of the V-shape or a bight of the U-shape, wherein the second legs respectively provide first and second arms of the shape of the element, and wherein the first legs either together provide a third arm of the shape or respectively provide third and fourth arms of the shape.

16. The absorbent article of claim 13, wherein the shape of the element is oriented so that first and second arms of the shape extend toward opposing lateral corner portions of a waist region of the absorbent article.

17. The absorbent article of claim 16, wherein the element defines the shape and the element is oriented so that a third arm of the shape extends substantially along a longitudinal line of the absorbent article, wherein the third arm is disposed toward a crotch portion of the absorbent article relative to the first and second arms.

18. The absorbent article of claim 16, wherein the element defines the shape and the element is oriented so that a third arm of the shape extends substantially along a central longitudinal line of the absorbent article, wherein the third arm is disposed toward a crotch portion of the absorbent article relative to the first and second arms.

19. The absorbent article of claim 13, wherein the element is a stiffening element, wherein arms of the shape of the element define a relatively collapse prone portion of the absorbent article between the arms as a result of a region of the absorbent article between the arms being less stiff than a region of the absorbent article covered by the arms of the stiffening element.

20. The absorbent article of claim 13, wherein the fastening element is a hook type fastener or an adhesive type fastener.

21. The absorbent article of claim 13, wherein the line of symmetry is arranged longitudinally with respect to the absorbent article.

* * * * *